United States Patent
Senia et al.

(10) Patent No.: US 6,261,099 B1
(45) Date of Patent: *Jul. 17, 2001

(54) METHOD AND APPARATUS FOR FILLING A ROOT CANAL OF A TOOTH

(75) Inventors: Steven S. Senia, San Antonio; William L. Wildey, Keller; Ennio S. Senia, San Antonio, all of TX (US)

(73) Assignee: Lightspeed Technology, Inc., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,528

(22) Filed: Apr. 7, 1998

Related U.S. Application Data

(60) Provisional application No. 60/042,787, filed on Apr. 7, 1997.

(51) Int. Cl.$^7$ .................................................. A61C 5/02
(52) U.S. Cl. ............................................... 433/224; 433/81
(58) Field of Search .............................. 433/81, 102, 224

(56) References Cited

U.S. PATENT DOCUMENTS

| | | | |
|---|---|---|---|
| 3,863,345 | * | 2/1975 | Malmin . |
| 3,908,270 | * | 9/1975 | Fishman ............................ 433/224 |
| 4,457,710 | * | 7/1984 | McSpadden ......................... 433/81 |
| 4,480,996 | * | 11/1984 | Crovatto ............................ 433/81 |
| 4,758,156 | * | 7/1988 | Johnson ............................. 433/81 |
| 4,894,011 | * | 1/1990 | Johnson ............................. 433/81 |
| 5,083,923 | * | 1/1992 | McSpadden ......................... 433/81 |
| 5,094,298 | * | 3/1992 | Johnson ............................. 433/81 |
| 5,275,562 | * | 1/1994 | McSpadden ........................ 433/224 |
| 5,286,193 | * | 2/1994 | Roanne .............................. 433/81 |
| 5,302,129 | * | 4/1994 | Heath et al. ........................ 433/81 |
| 5,350,298 | * | 9/1994 | Delaire ............................... 433/81 |
| 5,605,460 | * | 2/1997 | Heath et al. ....................... 433/224 |

FOREIGN PATENT DOCUMENTS 2 034 174 U * 1/1972 (DE) ................................ 433/102

* cited by examiner

*Primary Examiner*—Ralph A. Lewis
(74) *Attorney, Agent, or Firm*—Jackson Walker LLP

(57) ABSTRACT

A method of filling a root canal of a tooth includes inserting a plug of filling material into the root canal until a tip of the plug resides substantially at the apical foramen of the root canal and delivering a filling material into a remaining exposed portion of the root canal. An instrument for delivering a plug of filling material into a root canal of a tooth includes a shaft and a head formed integrally with the shaft, wherein the head includes a tip for receiving a plug of filling material. An instrument for delivering filling material into a root canal of a tooth includes a shaft and a working portion formed integrally with the shaft for carrying the filling material.

9 Claims, 4 Drawing Sheets

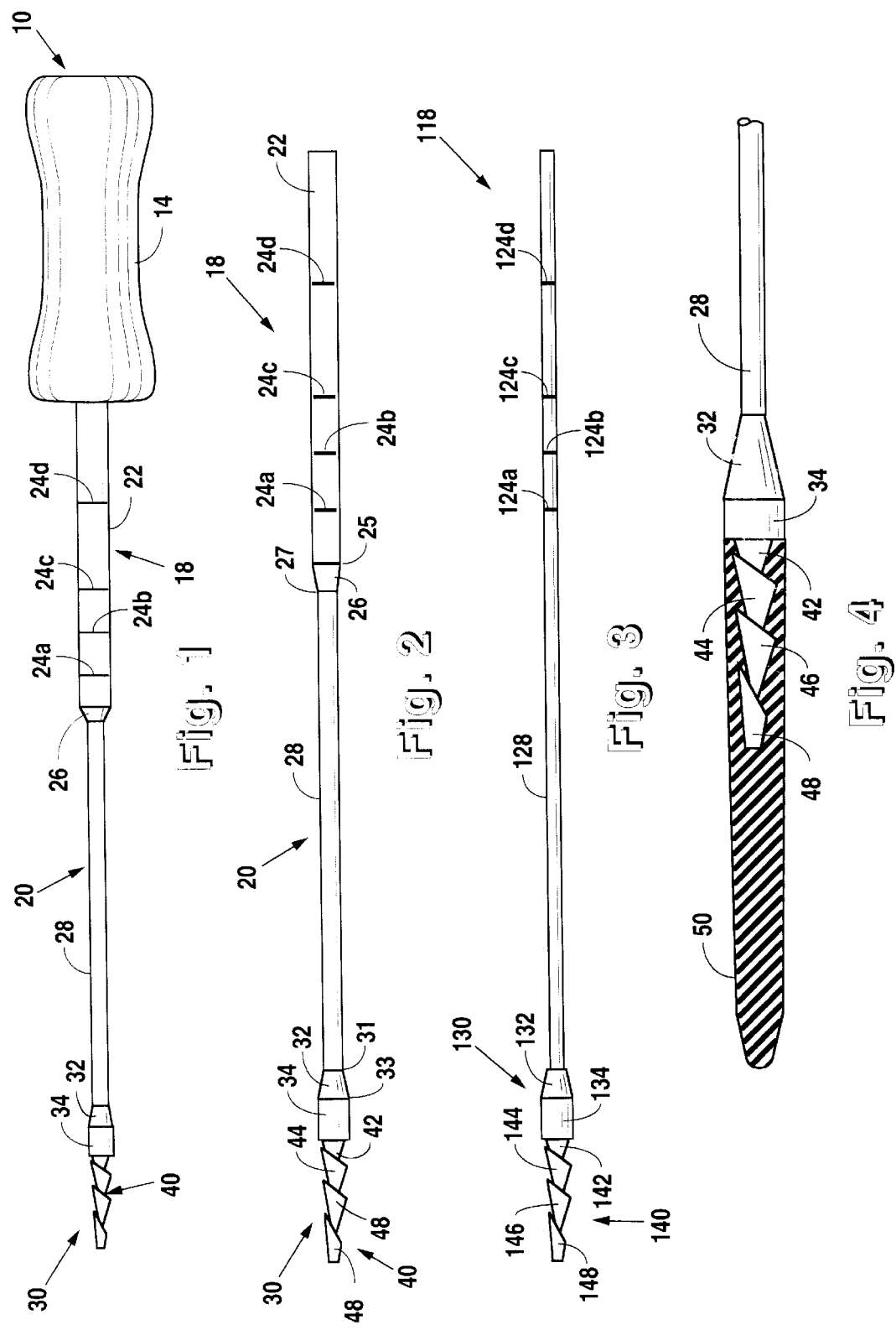

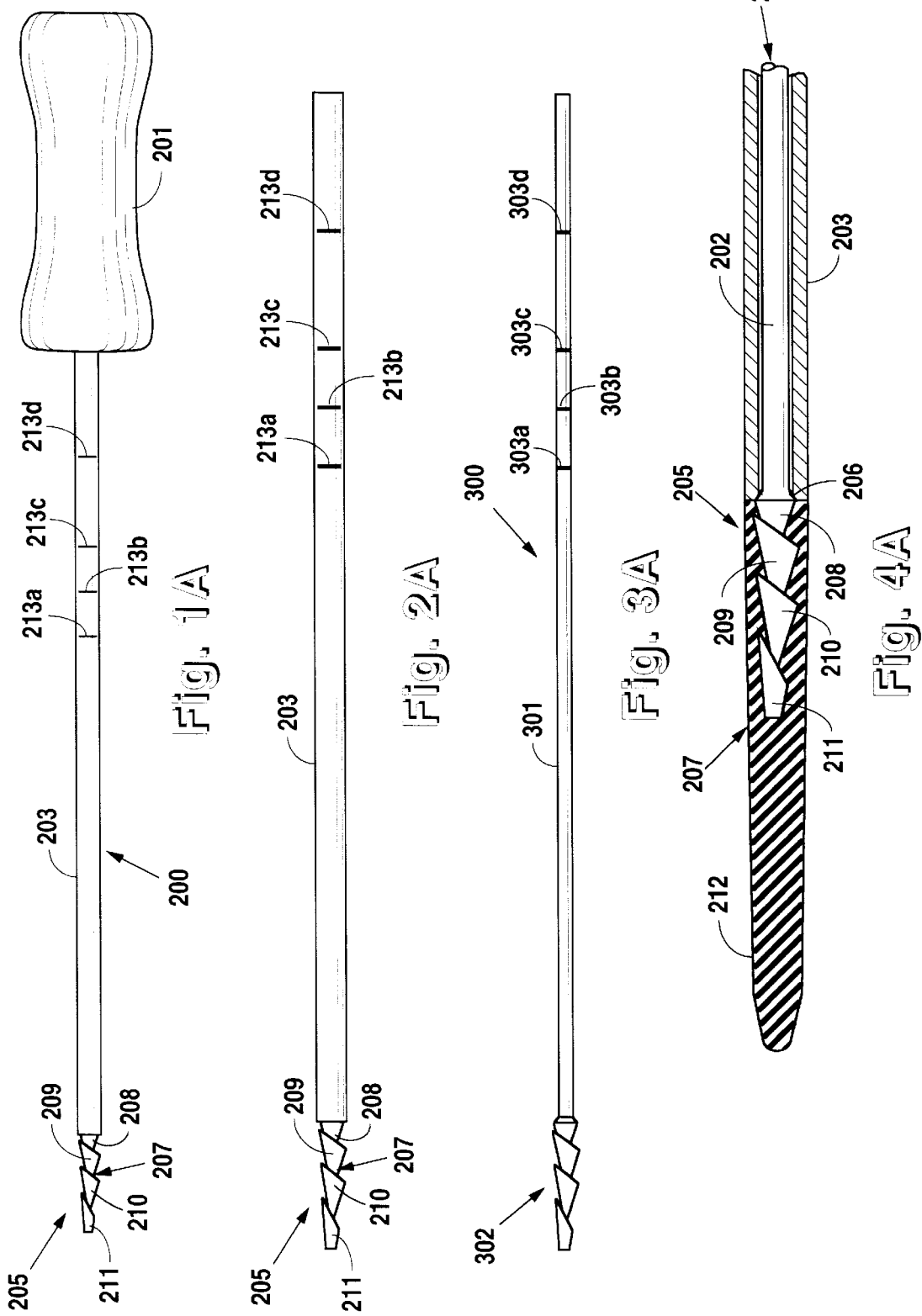

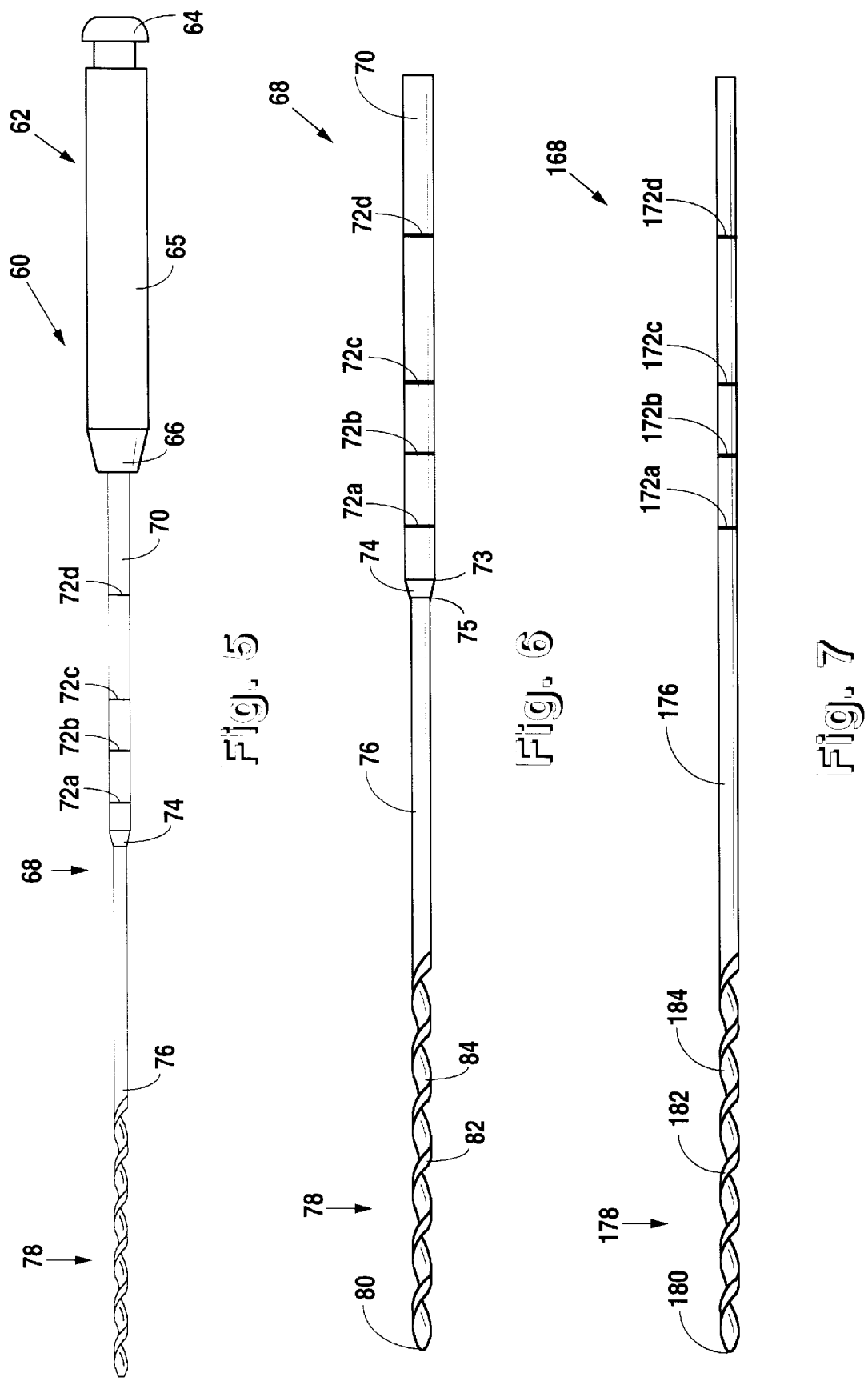

METHOD AND APPARATUS FOR FILLING A ROOT CANAL OF A TOOTH

This appln claims benefit of Provisional No. 60/042,787 filed Apr. 7, 1997.

BACKGROUND OF THE INVENTION

1. Field of the Invention

The present invention relates to root canal therapy and, more particularly, but not by way of limitation to a method and apparatus for filling a root canal of a tooth.

2. Description of the Related Art

Root canal therapy is a well-known dental procedure. The procedure includes removing a top portion of a diseased tooth, cleaning the tooth's root canals and pulp portion, filling the extirpated root canals with a rubbery compound, such as gutta percha, and cementing a crown to the tooth.

The root canal of the tooth extends from the pulp chamber to a tip, which is known as the apical foramen, of the tooth's root. In addition, the walls of the root canal form fissures and voids. It is desired to fill these fissures and voids as well as the main root canal during the filling process.

One method of filling the extirpated root canal utilizes a solid cone of gutta percha, which is known as the master cone. The master cone is placed within the root canal. Smaller cones, called accessory cones, are positioned around the master cone completing the filling of the root canal.

Another method of filling the root canal utilizes warmed gutta percha. This warmed gutta percha is injected into an extirpated root canal and allowed to cool completing the filling of the canal.

However, these methods suffer several disadvantages, namely overfilling and underfilling the root canal. An overfill occurs by positioning the master cone of gutta percha or injecting warmed gutta percha past the apical foramen into the surrounding bone and tissue. This positioning of the gutta percha may irritate the bone and periodontal ligament surrounding the tooth.

An underfill occurs with a gutta percha cone by failing to get the cone tip to the apical foramen of the tooth. Using warm gutta percha may also result in underfilling the root canal. Warmed gutta percha flows well in large cavities, but not in small cavities, such as the cavity near the root's apical foramen and the fissures and voids extending from the canal. As a result, using warmed gutta percha requires gutting of the tooth to enlarge the root canal for increasing the flowability of the gutta percha. The gutting of the tooth weakens the root potentially leading to future root fractures.

In addition to the problems of overfill and underfill, both procedures extend the procedure time for filling the root canal.

Accordingly, a method for filling root canals that eliminates overfill and underfill and decreases the procedure time will improve over conventional root canal fill methods.

SUMMARY OF THE INVENTION

In accordance with the present invention, a method of filling a root canal includes measuring the prepared diameter size of the root canal, comparing the prepared diameter size of the root canal to the diameter sizes of a plurality of different sized plugs of filling material, and selecting the plug of filling material providing a substantial match. Each plug of the plurality of different sized plugs of filling material is attached to a carrier instrument.

Once a plug of filling material has been selected, the selected plug is delivered into the root canal utilizing the carrier instrument. The plug of filling material is then detached from the carrier instrument when a tip of the plug resides substantially at the apical foramen of the root canal.

After the delivery of plug of filling material into the root canal, a working portion of a fill instrument is coated with a filling material. The fill instrument is inserted into the root canal until the end of the working portion contacts the plug of filling material, and, then, the fill instrument is spun during its removal from the root canal to deliver the filling material into a remaining exposed portion of the root canal.

An instrument for delivering a plug of filling material into a root canal includes a shaft and a head formed integrally with the shaft. The head includes a tip for receiving a plug of filling material. A handle may be attached to the shaft, and a sleeve may surrounding the shaft such that it abuts the plug of filling material to prevent the driving of the tip of the shaft further into the filling material during the delivery of the plug of filling material into the root canal.

An instrument for delivering filling material into a root canal includes a shaft and a working portion formed integrally with the shaft for carrying the filling material. The working portion has a length of from 0.25 mm to 15 mm in order to avoid overflowing the tooth with filling material. The working portion includes a helical member that defines a helical flute and that terminates in a rounded tip.

It is, therefore, an object of the present invention to provide a method for filling root canals that eliminates overfill and underfill and is faster than conventional methods.

Another object of the present invention is to provide a carrier instrument for positioning a plug of filling material such that a tip of the plug resides substantially at the apical foramen of a root.

A still further object of the present invention is to provide a dental fill instrument for augering filling material into the root canal.

Still other objects, features, and advantages of the present invention will become evident to those skilled in the art in light of the following.

BRIEF DESCRIPTION OF THE DRAWINGS

FIGS. 1 and 1A are side, elevational views of carrier instruments according to the preferred embodiment.

FIGS. 2 and 2A are side, elevational views of first embodiments of shafts for the carrier instruments.

FIGS. 3 and 3A are side, elevational views of second embodiments of shafts for the carrier instruments.

FIGS. 4 and 4A are side, elevational views of tips for the carrier instruments having a plug of filling material mounted thereon.

FIG. 5 is a side, elevational view of a fill instrument.

FIG. 6 is a side, elevational view of a first embodiment of a shaft of the fill instrument.

FIG. 7 is a side, elevational view of a second embodiment of a shaft of the fill instrument.

DETAILED DESCRIPTION OF THE PREFERRED EMBODIMENTS

Figure 8:
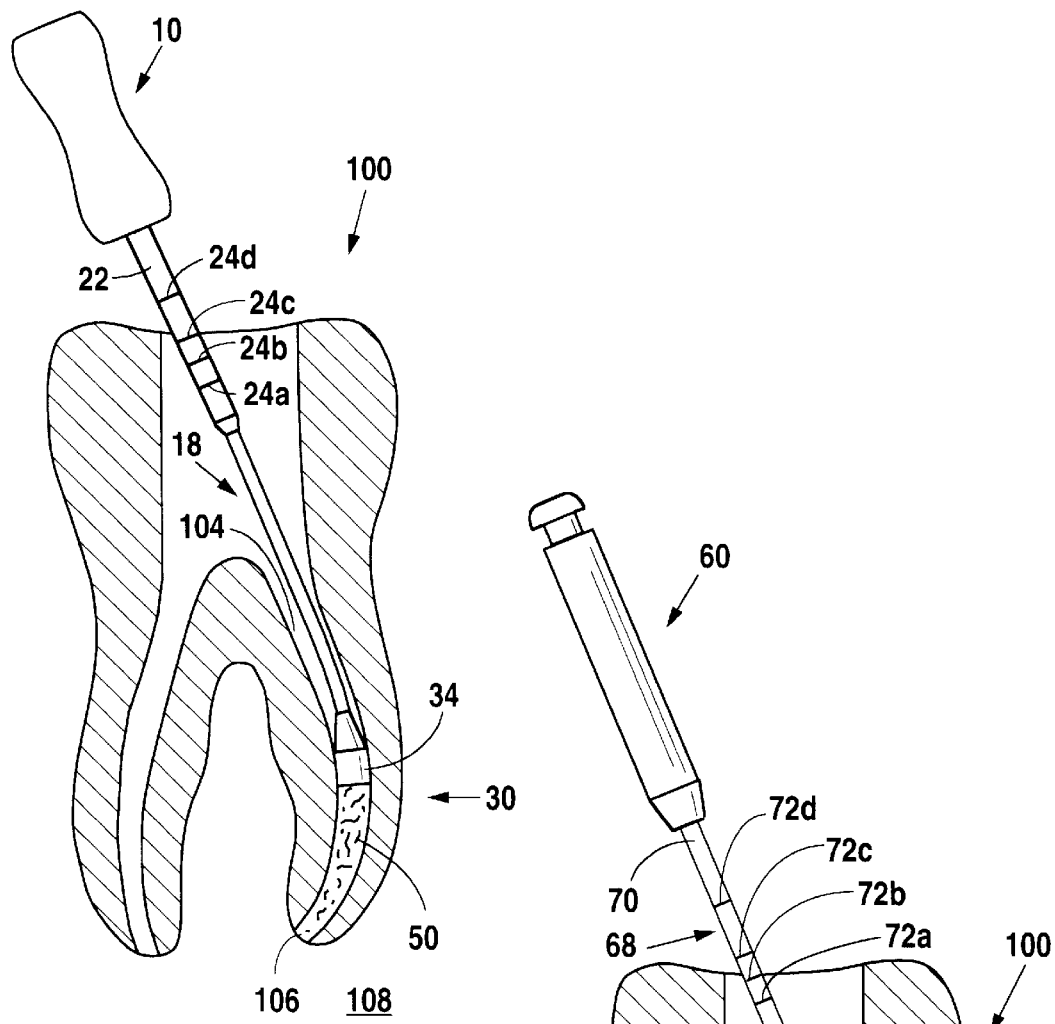
FIG. 8 is a elevational, cross-sectional view of a tooth having the carrier instrument inserted within a root canal.

Two devices are utilized in one preferred method of the present invention. One device, illustrated in FIGS. 1–4 and 1A–4A, is a carrier instrument 10 or 200 and the other device, illustrated in FIGS. 5–7, is a fill instrument 60. These instruments 10 or 200 and 60 may be constructed from commonly used dentistry materials, such as alloys of nickel and titanium, stainless steel, or hardened plastics.

The carrier instrument 10 includes a handle 14 connected to a shaft 18 using any suitable means such as press fitting. The handle 14 permits manual manipulation of the instrument 10. However, in other preferred embodiments the handle 14 may be replaced with a coupler.

The shaft 18 is sized to be received into a root canal of a tooth and includes a shank 20 and a head 30. The shank 20 includes a body 22, a tapered portion 26, and a neck 28. The body 22, preferably substantially cylindrical, may include markings 24a–d for determining the depth in the root canal of a solidified plug 50 of filling material, such as gutta percha. The body 22 has a diameter greater than the neck 28 for permitting markings 24a–d of sufficient size that are easily seen. The neck 28 is substantially cylindrical and has a long, slender construction that provides flexibility for maneuvering the head 30 through the curves and windings of the root canal, especially near the apical foramen. This flexibility of the neck 20 allows the placement of the solidified plug 50 of filling material, such as gutta percha, at the apical foramen (described herein). In this preferred embodiment, the plug 50 is cone shaped although other shapes may be utilized.

The frustro-shaped tapered portion 26 connects the body 22 with the neck 28 and has a first end 25 that has a diameter substantially equal to the body 22 and a second end 27 that has a diameter substantially equal to the neck 28. The first end 25 is formed integrally with the body 22 and the second end 27 is formed integrally with the neck 28.

The head 30 includes a tapered portion 32, a base 34, and a tip 40. The base 34 is substantially cylindrically shaped and has a diameter greater than the neck 28. The base 34 prevents the insertion of the plug 50 past the apical foramen of the tooth (described herein). The tapered portion 32, preferably frustum shaped, connects the base 34 with the neck 28 and has a first end 31 that has a diameter substantially equal to the neck 28 and a second end 33 that has a diameter substantially equal to the base 34. The first end 31 is formed integrally with the neck 28 and the second end 33 is formed integrally with the base 34.

The tip 40 includes a post 42, a first substantially frustro-conical barb 44, a second substantially frustro-conical barb 46, and a third substantially frustro-conical barb 48. The post 42 connects the barbs 42, 44, and 46 with the base 34 and is formed integrally with the base 34 at one end and the first barb 44 at an opposing end. The first barb 44 is formed integrally with the second barb 46 which, in turn, is formed integrally with the third barb 48. The barbs 44, 46, and 48 secure the solidified plug 50 of filling material, such as the gutta percha, that is placed on the barbs 44, 46, and 48 during manufacture of the carrier 10. The barbs 44, 46, and 48 screw into the plug 50 by rotating the instrument 10 clockwise. The barbs 44, 46, and 48 unscrew from the plug 50 by rotating the instrument 10 counter-clockwise.

A second embodiment of a shaft 118 is depicted in FIG. 3. The shaft 118 includes a neck 128 and a head 130. The neck 128 connects to the handle 14 using any suitable means such as press fitting and has markings 124a–d. The markings 124a–d permit determining the depth of the head 130 in the root canal. Extending the length of the neck 128 to the handle 14 provides greater flexibility for maneuvering the head 130 through the root canal. The head 130 is identical to the head 30 as previously described.

The carrier instrument 200 as illustrated in FIGS. 1A, 2A, and 4A includes a handle 201 connected to a shaft 202 and sleeve 203 using any suitable means such as press fitting. The handle 201 permits manual manipulation of the instrument 200. However, in other preferred embodiments the handle 201 may be replaced with a coupler.

The shaft 202 is similar to the shaft 18 and includes a shank 204 and a head 205. The shaft 202 resides in the sleeve 203 and is placed therein using any suitable means such as press fitting. The shank 204 is similar to the shank 20 and includes a body, a tapered portion, and a neck as previously described.

The head 205 includes a tapered portion 206 and a tip 207. The tapered portion 206, preferably frustum shaped, connects the tip 207 with the neck of the shank 204. The tip 207 includes a post 208, a first substantially frustro-conical barb 209, a second substantially frustro-conical barb 210, and a third substantially frustro-conical barb 211. The post 208 connects the barbs 209–211 with the tapered portion 206 and is formed integrally with the tapered portion 206 at one end and the first barb 209 at an opposing end. The first barb 209 is formed integrally with the second barb 210 which, in turn, is formed integrally with the third barb 211. The barbs 209–211 secure a solidified plug 212 of filling material, such as the gutta percha, that is placed on the barbs 209–211 during manufacture of the carrier 200. The barbs 209–211 screw into the plug 212 by rotating the instrument 200 clockwise. The barbs 209–211 unscrew from the plug 212 by rotating the instrument 200 counter-clockwise.

The sleeve 203 is sized to be received into a root canal of a tooth and functions to prevent the driving of the tip 207 further into the plug 212 during the placement of the plug 212 substantially at the apical foramen of the tooth. The sleeve 203 may include markings 213a–d for determining the depth of the sleeve 203 in the root canal. The sleeve is substantially cylindrical and has a long, slender construction that provides flexibility for maneuvering the head 205 through the curves and windings of the root canal, especially near the apical foramen. This flexibility allows the placement of a solidified plug 212 of filling material, such as gutta percha, at the apical foramen. In this preferred embodiment, the plug 212 is cone shaped although other shapes may be utilized.

A second embodiment of a shaft 300 is depicted in FIG. 3A. The shaft 300 includes a neck 301 and a head 302. The neck 301 connects to the handle 201 using any suitable means such as press fitting and has markings 303a–d. The markings 303a–d permit determining the depth of the head 302 in the root canal. Extending the length of the neck 301 to the handle 14 provides greater flexibility for maneuvering the head 302 through the root canal. The head 302 is identical to the head 205 as previously described. Although not shown, the shaft 300 may be press fit into a sleeve as previously described with reference to FIGS. 1A, 2A, and 4A.

The fill instrument 60 includes a coupler 62 attached to the shaft 68 using any suitable means such as press fitting. The coupler 62 includes a coupling 64, a body 65, and a tapered portion 66. The coupling 64 is insertable into a dental tool for machine operation and is formed integrally with the body 65. The body 65 is substantially cylindrical and is formed integrally with the tapered portion 66, which is preferably frustum-shaped. The coupler 62 is designed for machine operation, but in other preferred embodiments is replaced with the handle 14 for manual operation.

The shaft 68 is sized to be received into a root canal of a tooth and includes a body 70, a tapered portion 74, a neck 76, and a working portion 78. The body 70 is substantially cylindrical and formed integrally with the tapered portion 66 of the coupler 62. The body 70 has markings 72a–d for determining the depth of the working portion 78 in the root canal. The neck 76 is preferably cylindrical and has a smaller diameter than body 70 to provide flexibility to the instrument 60.

The tapered portion 74, preferably frustrum-shaped, connects the body 70 with the neck 76 and has a first end 73 and a second end 75. The first end 73, which has a diameter substantially equal to the diameter of the body 70, is formed integrally with the body 70 and the second end 75, which has a diameter substantially equal to the diameter of the neck 76, is formed integrally with the neck 76.

The working portion 78 is formed integrally with the neck 76 and has a helical member 82 that terminates in a rounded tip 80 and forms a helical flute 84. The rounded tip 80 prevents snagging of the root canal walls and damage to the plug 50 when inserting the fill instrument 60. The working portion 78 augers filling material, such as warmed gutta percha, into the root canal. The working portion 78 has a length of from 0.25 mm to 15 mm in order to avoid overflowing the tooth with filling material.

Another embodiment of the shaft 168 is depicted in FIG. 7. The shaft 168 includes a neck 176 formed integrally with a working portion 178. The extended neck 176 is attached to the coupler 60 using any suitable means such as press fitting. The extended length of the neck 176 provides greater flexibility to the shaft 168. The neck 176 includes markings 172a–d that perform the same function as previously described markings 72a–d. The working portion 178 is identical to the working portion 78 as previously described.

Figure 9:
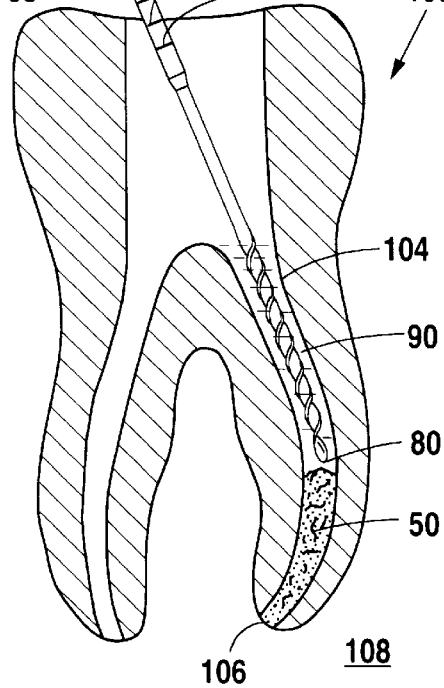
FIG. 9 is a elevational, cross-sectional view of the tooth having the fill instrument inserted within the root canal.

Referring to FIGS. 8–9, after the root canal 104 of a tooth 100 is extirpated, the carrier instrument 10 is inserted into the root canal 104. In this preferred embodiment the shaft 18 is utilized, but it should be understood that the shaft 118 may be used instead. The plug 50 inserts until a tip of the plug 50 resides substantially at the apical foramen of the root canal or the base 34 of the head 30 engages the walls of the canal 104. It is desired that the head 30 engage the wall when the tip of the plug 50 is positioned substantially at the apical foramen of the root canal. This engagement of the head 30 prevents overfilling of the canal 104 with filling material, such as gutta percha. The plug 50 may be inserted to the appropriate depth by referring to the markings 24a–d on the body 22.

If the plug 50 does not reside substantially at the apical foramen of the root canal or the head 30 of the carrier 10 is too large, the carrier instrument 10 may be withdrawn from the root canal 104. The barbs 44, 46 and 48 secure the plug 50 to the tip 40, thereby minimizing the risk of losing the plug 50 from the tip 40 in the root canal 104. Once the instrument 10 is withdrawn, another carrier instrument 10 having a smaller or larger sized head 30 and plug 50 is selected. This process may be repeated until a proper sized plug 50 is found. Alternatively, a proper sized plug 50 may be selected by measuring the prepared diameter size of the root canal and comparing the prepared diameter size of the root canal to the diameter sizes of carrier instruments 10 having smaller or larger sized plugs 50 to determine a substantial match.

Once a plug 50 of proper size is positioned such that the tip of the plug 50 resides substantially at the apical foramen 106 of the tooth 100, the carrier instrument 10 is rotated counter-clockwise. Rotating the instrument 10 unseats the plug 50 from the tip 40 by unscrewing the barbs 44, 46 and 48 from the plug 50. Once the plug 50 is unseated, the carrier instrument 10 is withdrawn.

Next, the fill instrument 60 is placed into a container of filling material or rolled on a flat surface containing filling material to coat the working portion 78 with the filling material. Afterwards, the fill instrument 60 is inserted into the root canal 104. In this preferred embodiment the shaft 68 is being used, but it should be understood that the shaft 168 may be used instead. The fill instrument 60 is inserted to the proper depth by checking the markings 72a–d or until the rounded tip 80 contacts the plug 50. The rounded tip 80 of the fill instrument 60 prevents snagging of the fill instrument 60 on the walls of the root canal 104 or the plug 50 during insertion.

Once the fill instrument 60 is at the preferred depth, it is rotated to auger the filling material 90, such as warmed gutta percha, into the root canal 104. The fill instrument 60 augers the filling material, such as warmed gutta percha, into the root canal 104 to fill all associated voids and fissures. The placement of the plug 50 such that the tip of the plug 50 resides substantially at the apical portion of the root canal allows the fill instrument 60 to be positioned in the root canal above the plug 50. The root canal 104 of a tooth 100 usually follows a winding path, especially near the apical portion of the root. Placing a shaft of an instrument into the canal 104 near the apical foramen 106 and rotating it risks breaking the shaft or scraping the walls of the canal 104. Therefore, the placement of the plug 50 prevents these hazards associated with conventional methods.

As the instrument 60 is spun, it is withdrawn as the canal fills with the filling material, such as warmed gutta percha. The plug 50 prevents the seepage of the filling material, such as warmed gutta percha, into surrounding tissue 108. Once the root canal 104 is filled, the fill instrument 60 is withdrawn. Other root canals in the tooth 100 are filled by the previously described steps to complete the filling process. Although the preferred method for delivering filling material into the root canal employs the instrument 60, a syringe containing filling material may be used, or, as those of ordinary skill in the art will recognize, other well known methods and apparatus for delivering filling material into the root canal may be utilized.

Although the present invention has been described in terms of the foregoing embodiment, such description has been for exemplary purposes only, and as will be apparent to those of ordinary skill in the art, many alternatives, equivalents, and variations of varying degrees will fall within the scope of the present invention. That scope, accordingly, is not to be limited in any respect by the foregoing description, rather, it is defined only by the claims that follow.

We claim:

1. A method of filing a root canal of a tooth, comprising the steps of:

providing an instrument having a first end and a barbed second end with a flexible shaft therebetween and including a resilient and flexible plug of filing material removably attached to the barbed second end of the instrument;

inserting the resilient and flexible plug of filing material utilizing the instrument into a lower portion oft he root canal until a tip of the resilient and flexible plug closes the apical foramen of the root canal and frictionally contacts the lower walls of the root canal coronal from the apical foramen;

detaching and removing the entire instrument from the resilient and flexible plug thereby placing the resilient and flexible plug of filing material as one piece in the lower portion of the root canal with the tip of the resilient and flexible plug closing the apical foramen of the root canal; and, delivery a filing material into a remaining exposed portion of the root canal.

2. The method according to claim 1 wherein the step of delivering a filling material into a remaining exposed portion of the root canal, comprises the steps of:

coating a working portion of a fill instrument with a filling material;

inserting the fill instrument into the root canal until the end of the working portion contacts the resilient and flexible plug of filling material; and spinning the fill instrument while removing it from the root canal to deliver the filling material into a remaining exposed portion of the root canal.

3. The method according to claim 1 further comprising, providing a plurality of instruments each having a first end and a barbed second end and each including a different sized resilient and flexible plug of filling material removably attached to a second end.

4. The method according to claim 3 further comprising, selecting an instrument from the plurality of instruments including a different sized resilient and flexible plug of filling material removably attached thereto such that a tip of the selected resilient and flexible plug of filling material closes the apical foramen of the root canal.

5. The method according to claim 4 wherein the step of selecting an instrument from the plurality of instruments including a different sized resilient and flexible plug of filing material removably attached thereto, comprises the steps of:

measuring the prepared diameter size of the root canal; and comparing the prepared diameter size of the root canal to the diameter sizes of the plurality of different sized plugs of filling material to determine a substantial match.

6. An instrument for delivering a resilient and flexible plug of filling material into a root canal of a tooth, comprising:

a flexible shaft having a first end and a barbed second end; and a head formed integrally with the second end of the shaft, the head including a tip for receiving a resilient and flexible plug of filling material, wherein the tip is detachable from the plug to remove the entire instrument from the resilient and flexible plug, thereby permitting the placement of the plug of filling material as one piece in the lower portion of the root canal with the tip of the plug closing the apical foramen of the root canal.

7. The instrument according to claim 6 further comprising a handle attached to the first end of the shaft.

8. The instrument according to claim 6 further comprising a sleeve surrounding the shaft.

9. The instrument according to claim 8 wherein the sleeve abuts the resilient and flexible plug of filling material to prevent the driving of the tip of the shaft further into the resilient and flexible plug of filling material during the delivery of the plug of filling material into the root canal.

* * * * *